United States Patent
Thakker et al.

(10) Patent No.: US 10,653,713 B2
(45) Date of Patent: May 19, 2020

(54) METHODS FOR DISTRIBUTING AGENTS TO AREAS OF BRAIN

(75) Inventors: Deepak Ramesh Thakker, Blaine, MN (US); Lisa L. Shafer, Stillwater, MN (US); Greg Stewart, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 1286 days.

(21) Appl. No.: 13/267,243

(22) Filed: Oct. 6, 2011

(65) Prior Publication Data

US 2012/0087869 A1     Apr. 12, 2012

Related U.S. Application Data

(60) Provisional application No. 61/390,266, filed on Oct. 6, 2010, provisional application No. 61/405,363, filed on Oct. 21, 2010.

(51) Int. Cl.

| | |
|---|---|
| *A61K 9/00* | (2006.01) |
| *A61K 31/711* | (2006.01) |
| *A61K 49/10* | (2006.01) |
| *A61K 49/14* | (2006.01) |
| *A61M 5/168* | (2006.01) |
| *A61M 5/142* | (2006.01) |

(52) U.S. Cl.
CPC .......... *A61K 31/711* (2013.01); *A61K 49/105* (2013.01); *A61K 49/143* (2013.01); *A61M 5/14276* (2013.01); *A61M 5/16804* (2013.01); *A61M 2205/50* (2013.01); *A61M 2210/0693* (2013.01)

(58) Field of Classification Search
CPC .................................................. A61K 31/711
See application file for complete search history.

(56) References Cited

U.S. PATENT DOCUMENTS

| | | |
|---|---|---|
| 4,650,675 A | 3/1987 | Borel |
| 7,052,486 B2* | 5/2006 | Hildebrand .................. 604/502 |
| 7,182,944 B2 | 2/2007 | Bankiewicz |
| 7,371,225 B2 | 5/2008 | Oldfield |
| 2002/0052311 A1 | 5/2002 | Solomon |
| 2004/0220546 A1* | 11/2004 | Heruth et al. ................ 604/508 |
| 2012/0022031 A1* | 1/2012 | Boyd ............................ 514/171 |

FOREIGN PATENT DOCUMENTS

WO    WO 2011/008982     1/2011

OTHER PUBLICATIONS

Boado et al., "Fusion Antibody for Alzheimer's Disease with Bi-Directional Transport Across the Blood-Brain Barrier and Abeta Fibril Disaggregation," *Bioconjug Chem*, 2007; 18(2):447-455.

(Continued)

*Primary Examiner* — Paul Dickinson
(74) *Attorney, Agent, or Firm* — Mueting Raasch Group

(57) ABSTRACT

Broad cerebrospinal fluid (CSF) distribution of an agent is achievable by delivering the agent in a liquid formulation to the CSF at flow rates less than 500 microliters per hour, such as between about 2 microliters per hour and about 100 microliters per hour.

19 Claims, 11 Drawing Sheets

(56) References Cited

OTHER PUBLICATIONS

Chauhan et al., "Effect of Age of the Duration and Extent of Amyloid Plaque Reduction and Microglial Activation After Injection of Anti-Aβ Antibody Into the Third Ventricle of TgCRND8 Mice," *Journal of Neuroscience Research*, 2004, 78:732-741.

Deane et al., "IgG-Assisted Age-Dependent Clearance of Alzheimer's Amyloid β Peptide by the Blood-Brain Barrier Neonatal Fc Receptor," *Neurobiology of Disease*, 2005, 25(5):11495-11503.

Pardridge, William M., "Molecular Trojan Horses for Blood-Brain Barrier Drug Delivery," *Current Opinion in Pharmacology* 2006, 6:494-500.

Rossi, John J., "Receptor-Targeted siRNAs,", *Nature Biotechnology*, 2005, vol. 23, No. 6, pp. 682-684.

Schlachetzki et al., "Expression of the Neonatal Fc Receptor (FcRn) at the Blood-Brain Barrier," *Journal of Neurochemistry*, 2002, 81:203-206.

Vornlocher, Hans-Peter, "Antibody-Directed Cell-Type Specific Delivery of siRNA," *Trends in Molecular Medicine*, 2006, vol. 12, No. 1, pp. 1-3.

Wilcock et al., "Passive Immunotherapy Against Aβ in Aged APP-Transgenic Mice Reverses Cognitive Deficits and Depletes Parenchymal Amyloid Deposits in Spite of Increased Vascular Amyloid and Microhemorrhage," *Journal of Neuroinflamation*, 2004, 1:24.

Wilcock et al., "Passive Amyloid Immunotherapy Clears Amyloid and Transiently Activates Mcroglia in a Transgenic Mouse Model of Amyloid Deposition," *The Journal of Neuroscience*, 2004, 24(27):6144-6151.

Bernards, "Cerebrospinal Fluid and Spinal Cord Distribution of Baclofen and Bupivacaine during Slow Intrathecal Infusion in Pigs", *Anesthesiology*, Jul. 2006; 105(1):169-78.

Flack et al., "Cerebrospinal Fluid and Spinal Cord Distribution of Hyperbaric Bupivacaine and Baclofen during Slow Intrathecal Infusion in Pigs", *Anesthesiology*, Jan. 2010; 112(1):165-73.

\* cited by examiner

METHODS FOR DISTRIBUTING AGENTS TO AREAS OF BRAIN

RELATED APPLICATIONS

This application claims the benefit of priority to U.S. Provisional Application Nos. 61/390,266 and 61/405,363, filed on Oct. 6, 2010 and Oct. 21, 2010, which applications are hereby incorporated herein by reference in their respective entireties to the extent that they do not conflict with the present disclosure.

FIELD

This disclosure relates to methods for delivering agents, such as therapeutic or diagnostic agents, to a brain; and, more particularly, to methods of achieving distribution of the agent to desired locations of the brain and spinal cord, collectively comprising the Central Nervous System (CNS).

BACKGROUND

A variety of agents have been administered to the cerebrospinal fluid (CSF), such as through intracerebroventricular (ICV) or intrathecal (IT) bolus infusion. Typically, these agents are administered acutely through a single, bolus infusion at flow rates in the range of about 0.5 to 12 ml/min. At such high delivery rates, the agents can achieve wider distribution within the central nervous system (CNS), albeit transiently.

However, at lower flow rates, such as less than 1 ml/day, studies report that the distribution of the agent in the CSF is limited. For example, one study reported the distribution of a small molecule agent within the CSF following IT infusion at a rate of 20 microliters per hour was limited to less than 5 cm of the spinal cord relative to the infusion site.

In many situations and for many reasons, it would be desirable to administer an agent at a low flow rate to a subject's CSF; e.g. when using a chronically implanted infusion device, but achieve broad distribution of the agent in the subject's CNS.

SUMMARY

The present disclosure presents results demonstrating that agents may be broadly distributed in a subject's CSF when delivered to the CSF at low flow rates, such as less than 1 ml per hour, less than 0.5 ml per hour, over prolonged periods of time. Prior studies at such low infusion rates concluded that CSF distribution is limited. However, as disclosed herein, broad CSF distribution is obtained with such low infusion rates. Further, broad distribution is achieved at low flow rates regardless of whether the infused molecule is a small molecule or a large molecule.

We demonstrate that a widespread distribution of small or large molecules can be achieved in the CSF and also into the CNS tissue upon administration of the molecules into the CSF at low flow rates, particularly for a duration that allows the establishment and maintenance of steady state levels in the CSF. Steady state refers to the scenario wherein the amount of molecule delivered into the CSF is equal to the amount of molecule cleared from the CSF, such that roughly constant levels of the molecule are maintained in the CSF at any given time. In this regard, the CSF turnover/production rate of the subject is an important factor in determining the time required to clear the administered molecule from the CSF, and thereby, also the time required to achieve steady state in the CSF.

In embodiments, a method for delivering a molecule to the cerebrospinal fluid (CSF) of a subject is described. The method includes administering a liquid formulation comprising the molecule directly to the CSF, for example to the intrathecal space of the subject at a flow rate of less than 500 microliters per hour. The liquid formulation may be administered at any suitable flow rate, such as less than 200 microliters per hour or between about 4 microliters per hour and about 100 microliters per hour, or between about 2 microliters per hour and about 25 microliters per hour. The molecule may have any suitable molecular weight, such as less than 5 kDa. (e.g., a small molecule), greater than 5 kDa (e.g., is not small), between about 5 kDa and about 15 kDa (e.g., a mid-sized biologic such as small peptides, antisense DNA, antisense RNA, and short interfering (si)RNA), between about 15 kDa and about 200 kDa (e.g., a large-sized biologic such as proteins and antibodies), or greater than about 200 kDa (e.g., a very large protein/biologic such as DNA, DNA-protein complexes, or virus, phage). The liquid formulation may be administered to the CSF in any suitable manner, such as via an implantable infusion device. In some embodiments, the liquid formulation is introduced into the subject's CSF via a catheter. The catheter may have a delivery region through which the molecule is configured to exit, and the delivery region may be positioned in a lumbar, thoracic, or cervical region of the subject's spinal intrathecal space, the cerebral ventricles, the subdural space (for example overlying the cerebral cortex), or any other place where CSF may be safely accessed.

In embodiments, a method for delivering a molecule to CSF of a brain of a subject is described. The method includes administering a liquid formulation comprising the molecule to a CSF-containing space of the subject at a flow rate of less than 500 microliters per hour. The liquid formulation may be administered at any suitable flow rate, such as less than 200 microliters per hour or between about 4 microliters per hour and about 100 microliters per hour or between about 2 microliters per hour and about 25 microliters per hour. The molecule may have any suitable molecular weight, such as less than 5 kDa, greater than 5 kDa, between about 5 kDa and about 15 kDa, between about 15 kDa and about 200 kDa, or greater than about 200 kDa. The liquid formulation may be administered to the CSF in any suitable manner, such as via an implantable infusion device. In some embodiments, the liquid formulation is introduced into the subject's intrathecal space via a catheter. The catheter may have a delivery region through which the molecule is configured to exit, and the delivery region may be positioned in a lumbar, thoracic or cervical region of the subject's spinal canal.

In embodiments, a method for broadly distributing a molecule in the CSF of a subject. The method includes administering a liquid formulation comprising the molecule to a CSF-containing space of the subject at a flow rate of less than 500 microliters per hour.

In embodiments, the present disclosure describes a method for broadly distributing a molecule in the CSF of a subject. The method includes administering a fluid composition comprising the molecule to the subdural or epidural space of the subject at a flow rate of less than 500 microliters per hour.

In embodiments, systems described herein include implantable infusion devices configured, or programmed with instructions, to carryout the methods described herein.

One or more embodiments described herein present one or more advantages over existing devices, systems and methods for achieving broad distribution of a molecule in a patient's CSF. For example, achieving broad CSF distribution of a molecule at low flow rates allows one to realize advantages associated with implantable infusion devices, which are capable of delivering at flow rates of less than 500 microliters per hour. Additionally, molecules can be delivered to the brain via intrathecal administration at such low flow rates, avoiding the need to penetrate brain tissue associated with ICV or intraparenchymal (IPA) delivery. These and other advantages will be evident to those of skill in the art upon reading the disclosure presented herein.

BRIEF DESCRIPTION OF THE DRAWINGS

FIGS. 7A and 7C show the monkey prior to administration of the Gd-DTPA.

FIG. 10D is a view of a different slice of the brain of the image presented in FIG. 10C; and FIG. 10E is a view of the relatively caudal spinal region of the image presented in FIG. 10C.

Figure 1:
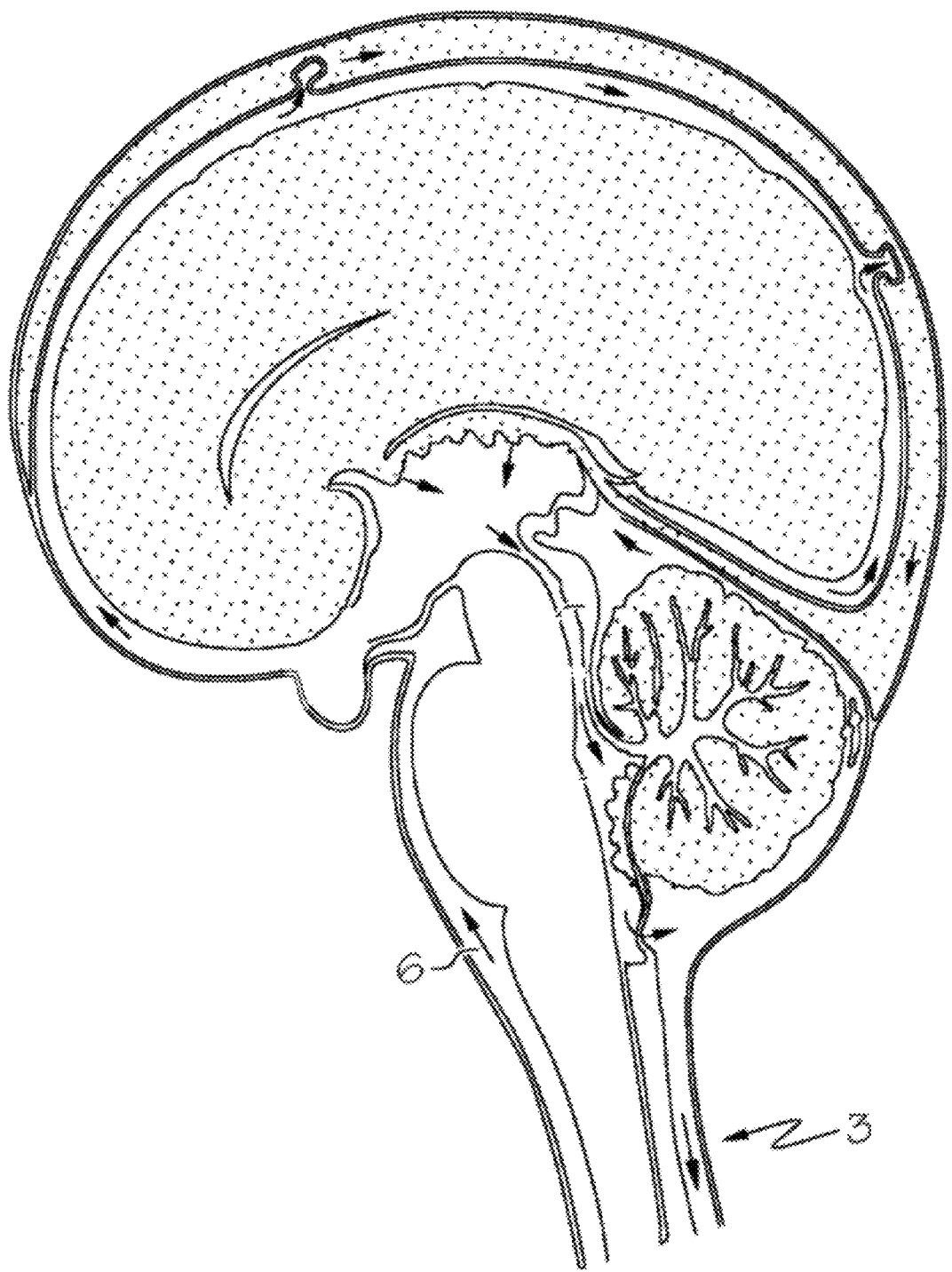
FIG. 1 is a schematic drawing of a section of a brain and portions of a spinal cord showing cerebrospinal fluid flow.

The schematic drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

The following description illustrates various embodiments. It is to be understood that other embodiments are contemplated and may be made without departing from the scope or spirit of the present invention. Thus, the following description is not to be taken in a limiting sense.

All scientific and technical terms used in this application have meanings commonly used in the art unless otherwise specified. The definitions provided herein are to facilitate understanding of certain terms used frequently herein and are not meant to limit the scope of the present disclosure.

As used herein, the singular forms "a", "an", and "the" encompass embodiments having plural referents, unless the content clearly dictates otherwise.

As used herein, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to".

As used herein, the terms "treat" or the like means alleviating, slowing the progression, preventing, attenuating, or curing the treated disease.

As used herein, "disease", "disorder", "condition" or the like, as they relate to a subject's health, are used interchangeably and have meanings ascribed to each and all of such terms.

As used herein, "subject" means a mammal to which an agent is administered for the purposes of treatment or investigation. Mammals include mice, rats, cats, guinea pigs, hamsters, dogs, sheep, monkeys, chimpanzees, and humans.

As used herein, a "liquid formulation of a molecule" is a composition that contains the molecule and that is liquid at room temperature and at 37° C.

As used herein, an "interfering RNA molecule" is a synthetic, double-stranded oligoribonucleotide that selectively contributes to the degradation of endogenous or pathogenic target RNA and reduces levels of the corresponding protein. Interfering RNA molecules (iRNAs) typically have a molecular weight between about 5 kDa and 15 kDa. WO 2011/008992 describes additional details regarding iRNAs, which PCT publication is hereby incorporated herein by reference in its entirety to the extent that it does not conflict with the disclosure presented herein. In embodiments described herein, a molecule in a liquid formulation is any molecule other than an iRNA.

As used herein, an "iRNA configured to inhibit expression of a Huntington protein" is an iRNA that, when introduced to or into a cell, tissue, subject, or the like that expresses a Huntington protein, results in decreased levels of the Huntington protein. WO 2011/008992 describes additional details regarding Huntington proteins, which PCT publication is hereby incorporated herein by reference in its entirety to the extent that it does not conflict with the disclosure presented herein. In embodiments described herein, a molecule in a liquid formulation is any molecule other than an iRNA configured to inhibit expression of a Huntington protein.

The present disclosure relates to achieving broad distribution of molecules in CSF of a subject by delivering the molecules in a liquid formulation at a flow rate of less than 1 ml per hour, such as less than 500 microliters per hour and for a duration that is up to or longer than that required to achieve steady state (the latter may be approximated based on the known turnover rate of CSF). Prior studies of such low infusion rates concluded that CSF distribution is extremely limited. However, as disclosed herein, broad CSF distribution is obtained with these low infusion rates. Further, broad distribution is achieved at low flow rates regardless of whether the infused molecule is a small molecule or a large molecule.

According to various embodiments, a liquid formulation containing a molecule of interest may be delivered directly to cerebrospinal fluid 6 of a subject. Referring to FIG. 1, cerebrospinal fluid (CSF) 6 exits the foramen of Magendie and Luschka to flow around the brainstem and cerebellum. The arrows within the subarachnoid space 3 in FIG. 2 indicate cerebrospinal fluid 6 flow. The subarachnoid space 3 is a compartment within the central nervous system that contains cerebrospinal fluid 6. The cerebrospinal fluid 6 is produced in the ventricular system of the brain and communicates freely with the subarachnoid space 3 via the foramen of Magendie and Luschka. A liquid formulation including a molecule of interest may be delivered to cerebrospinal fluid 6 of a subject anywhere that the cerebrospinal fluid 6 is accessible. For example, the composition may be administered intrathecally (e.g., at a lumbar, sacral, thoracic or cervical level or into the cisterna magna), intracerebroventricularly, or the like. In some embodiments, the fluid composition is administered subdurally, for example by delivery of drug to the CSF over the cortical convexities of the brain.

Any suitable molecule may be delivered. The results presented in the Examples herein below illustrate that the molecule may be of any suitable size. It is envisioned that a small molecule (less than about 5 kDa) or large molecule (greater than about 5 kDa) may be administered to the CSF at low flow rates to achieve broad CSF distribution. It is contemplated that various classes of large molecules may be administered. For example, mid-sized biologics such as polypeptides, larger-sized biologics such as antibodies, and even larger sized biologics such as proteins may be administered at low flow rates into the CSF to achieve broad distribution. As used herein, "broad distribution" means that a molecule is distributed generally throughout most, if not all, of the region of interest. For example, if brain CSF is the region of interest, then the molecule will be generally distributed throughout the CSF compartments in and surrounding the brain. If the CSF in general is the region of interest, a molecule delivered to a specific location of the CSF is considered to be broadly distributed in the CSF if, after delivery, the molecule is present throughout the CSF.

The molecule may be a therapeutic agent, a diagnostic agent, or the like. In general, a therapeutic agent is an agent intended to treat a disease, while a diagnostic agent is an agent intended to aid in identifying a condition or disease of a subject, the presence or absence of a molecule in a subject, or the like. For example, the molecule may be any known or future developed small molecule or biologic therapeutic agent. Examples of biologic therapeutic agents that may be employed in accordance with the teachings presented herein include antibodies or fragments thereof; inhibitory RNA molecules such as antisense RNA, microRNA (miRNA), small interfering RNA (siRNA), or the like; DNA; polypeptides; proteins; viruses, vectors or the like. The molecules may be used for therapeutic, diagnostic or investigatory purposes.

Generally, the molecules will be formulated into a liquid formulation suitable for delivery to the CSF. The formulation may include the molecule and a variety of other pharmaceutically acceptable components. See Remington's Pharmaceutical Science (15th ed., Mack Publishing Company, Easton, Pa. (1980)). The preferred form may depend on the intended application. The formulations may also include, depending on the formulation desired, pharmaceutically-acceptable, non-toxic carriers or diluents, which are defined as vehicles commonly used to formulate pharmaceutical compositions for animal or human administration. In most cases, the diluent is selected so as not to adversely affect the activity of the molecule of interest. Examples of such diluents are distilled water, physiological phosphate-buffered saline, artificial cerebrospinal fluid, citrate buffered saline, Ringer's solutions, dextrose solution, and Hank's solution.

Typically the liquid formulations are formed as injectable compositions. Injectable compositions include solutions, suspensions, dispersions, or the like. Injectable solutions, suspensions, dispersions, or the like may be formulated according to techniques well-known in the art (see, for example, Remington's Pharmaceutical Sciences, Chapter 43, 14th Ed., Mack Publishing Co., Easton, Pa.), using suitable dispersing or wetting and suspending agents, such as sterile oils, including synthetic mono- or diglycerides, and fatty acids, including oleic acid.

Proper fluidity of solutions, suspensions or dispersions may be maintained, for example, by the formation of liposomes, by the maintenance of the desired particle size, in the case of dispersion, or by the use of nontoxic surfactants.

The prevention of microorganisms can be accomplished by heat sterilization or filter sterilization, whichever is compatible with the molecule and formulation being used. Isotonic agents such as sugars, buffers, or sodium chloride may be included. Solubility enhancers may be added.

In various embodiments, the final formulation is adjusted to have a pH between about 4 and about 9, between about 5 and about 7, between about 5.5 and about 6.5, or about 6. The pH of the composition may be adjusted with a pharmacologically acceptable acid, base or buffer. Hydrochloric acid is an example of a suitable acid, and sodium hydroxide is an example of a suitable base. The hydrochloric acid or sodium hydroxide may be in any suitable form, such as a 1N solution In various embodiments, a resultant fluid composition contains an amount of one or more molecules effective to treat a disease to allow meaningful study of a subject to which the composition is administered at a particular flow rate. The effective amount of the molecule to be administered will vary depending on the molecule itself and the disease to be treated. The amount may also vary depending on the subject to which it is administered and the location of administration (e.g., IT vs. ICV).

The liquid formulation containing the molecule of interest may be administered to the CSF in any suitable manner. In various embodiments, a system including an infusion device is used to deliver a liquid formulation containing a molecule of interest to subject. The system may further include a catheter operably coupled to the infusion device. The infusion device may include a drive mechanism or pump, such as a piston pump, peristaltic pump, positive pressure reservoir, or the like. Non-limiting examples of infusion devices include osmotic pumps, fixed-rate pumps, programmable pumps and the like. Each of the aforementioned pump systems contains a reservoir for housing the fluid composition and an outlet in fluid communication with the reservoir. The catheter may be operably coupled to the outlet. The catheter includes one or more delivery regions, through which the fluid may be delivered to one or more target regions of the subject. The infusion device may be implantable or may be placed outside the body via an externalized catheter outside the body, external to the subject. Alternatively an implanted port that is in direct communication with a CSF compartment via a catheter can be accessed on an intermittent basis and drug infused over the desired duration using an external pump delivering the drug at an appropriate rate as described herein.

The liquid formulation may be administered at any suitable rate to the subject's CSF to achieve broad distribution. In many embodiments, the composition is administered at a rate of less than 1 ml per hour, such as less than 500 microliters per hour. For example, the composition may be administered at a rate of less than 200 microliters per hour or between about 4 microliters per hour and 100 microliters per hour or between about 2 microliters per hour and 25 microliters per hour. It will be understood flow rates per hour may be converted to flow rates per minute, per second, per day, etc. using appropriate conversion factors and that, when properly converted, such flow rates are considered equivalent.

The infusion device may be configured to deliver the liquid formulation at these rates. By way of example, the infusion device may include electronics configured to control the rate at which the liquid formulation may be delivered from the reservoir to the outlet. In embodiments, the electronics are programmed with instructions that cause the liquid formulation to be delivered at the desired rates.

Based on the EXAMPLES provided below, it has been found that for Rhesus monkeys a constant flow rate of greater than about 0.1 ml/day of an agent into the CSF over a period of 1 through 3 days was sufficient to cause wide distribution in the CSF. For example, flow rates of between 0.4 ml/day and 2.4 ml/day over a period of 1 through 3 days were effective in broadly distributing agents throughout the CSF. Further, flow rates in the range of 0.048 ml/day and 0.1 mL/day also distributed the test articles in the CSF given sufficient time for infusion to allow for test article levels in the CSF to reach steady state. For example, the steady state distribution of Gd-DTPA infused intracerebroventricularly at 0.1 mL/day demonstrated a complete CSF coverage, and that infused at 0.048 mL/day was evident in the CSF compartments in and around the brain, but not the spinal cord. Therefore, in addition to demonstrating that prolonged infusion at low flow rates can distribute the infused molecules widely into the CSF compartments, we also show the significance of selecting an appropriate flow rate for the desired extent of CSF distribution of the infused molecule.

We found that the molecular weight of an infused molecule also contributes towards its distribution within the CSF of Rhesus monkeys. In this case, steady state CSF levels of the infused molecule are subject to the size of the test article. For example, the test article of molecular weight ~600 Da, Gd-DTPA, distributed broadly throughout the CSF in and around the brain and spinal cord, when infused intracerebroventricularly at a flow rate of 0.1 mL/day for a period of 6 hours. Relative to the 600 Da Gd-DTPA, the distribution of 74,000 Da Gd-albumin was largely confined to the CSF in and around the brain, and not in the spinal cord. Consequently, flow rates for prolonged infusion of test articles can be selected based on the molecule's size to achieve the desired CSF coverage at steady state.

Further, we also demonstrate the significance of selecting an appropriate infusion site to achieve the desired distribution of the infused molecule. For example, ICV infusion at 0.4 mL/day resulted in a narrower distribution of Gd-albumin (74,000 Da) in the CSF over a period of 3 days, whereas intrathecal lumbar infusion at the same flow rate widely distributed the same molecule throughout the CSF within 1 day. Differences in CSF distribution upon ICV versus IT infusion were also evident with Gd-DTPA (600 Da), wherein ICV infusion at 0.1 mL/day flow rate provided complete CSF coverage for the molecule, while IT infusion confined the molecule in the IT space.

Collectively, our data reflect the importance of selecting a combination of factors, including the time to allow the infused test article to reach steady state, infusion target site, infusion flow rate, and the molecular weight of the molecule in order to achieve the predetermined distribution of the molecule in the CNS. Due to differences in CSF volume and turnover between monkey and humans some scaling may be desirable for achieving similar distribution of an agent in humans. Table 1 below provides some parameters of SCF in Rhesus monkeys and humans and provides some insights as to how scaling may be achieved.

TABLE 1

CSF parameters of Rhesus monkey and human

|  | CSF turnover/hr | Avg. CSF volume | Avg. turnover rate |
| --- | --- | --- | --- |
| Monkey | 16% | 13 ml | 2.1 ml/hr |
| Human | 16% | 125 ml | 20 ml/hr |

As shown in Table 1, the volume of the CSF of an average adult human is about 10 times greater than the volume of a mature Rhesus monkey. Accordingly, scaling in terms of flow rate may be increased about 10 fold in humans relative to Rhesus monkeys. That is, flow rates of greater than about 1 ml/day may be useful in broadly distributing an agent administered to CSF of a human. For example, flow rates of about 2 ml/day, 3 ml/day, 4 ml/day, 5 ml/day, 10 ml/day, 20 ml/day, or the like, or greater may be suitable for achieving broad distribution in humans. Such a scaling factor is supported by the fact that many humans receiving intrathecal morphine or baclofen at constant rates of 0.5 ml/day do not appear to suffer from any supraspinal side effects, suggesting that the drugs do not reach the brain in appreciable concentrations.

Alternatively, as the CSF turnover rate is similar between Rhesus monkeys and humans (see Table 1), it is possible that scaling on this basis (approximately 1:1) can achieve similar distribution in monkeys and humans—particularly if CSF turnover is a significant factor for movement of an agent throughout the CSF. However, to achieve a similar effect in humans and rhesus monkeys a 10 fold higher concentration of agent may be desired due to the difference in CSF volume, assuming similar distribution with similar flow rates.

Likely, appropriate scaling is somewhere between the two scenarios described above. For example, suitable flow rates of between 1 and 10 times higher in humans than in monkeys with corresponding concentrations of between 10 and 1 times higher in humans than in monkeys may result similar effects in humans with similar distribution between the two species.

Appropriate scaling between other species may be determined in a manner similar to that outlined above with regard to Rhesus monkeys and humans.

In any case, it may be desirable to limit the volume of therapeutic or diagnostic composition administered to the CSF of a subject to avoid adverse effects such as hydrocephalus or the like. For example, it may be desirable to limit the volume of therapeutic or diagnostic composition delivered per day to about 25% or less, about 20% or less, about 15% or less, or about 10% or less, about 5% or less, or about 2% or less of the CSF volume of the subject to which the composition is delivered. By way of example, 25% of the CSF volume of a typical adult human is about 30 ml, and 10% of the CSF volume is about 12.5 ml.

To achieve a suitable flow rate to achieve broad distribution while conserving on the amount or volume delivered, a therapeutic or diagnostic composition may be delivered to a subject's CSF in pulsatile or episodic manner, as a controlled and programmed therapy rather than at a constant rate. For example, a therapeutic agent may be administered at a sufficiently high flow rate and duration to achieve desired distribution within the CNS, and then the flow rate would be reduced to a very low level for a prolonged period of time (days to weeks) to conserve drug and also maintain patency of the catheter. This pattern may be repeated on a chronic basis. It will be understood that nearly any other pulsatile dosage regimen may be employed and that the regimens discussed above are merely examples.

In some embodiments, between about 10 ml and 100 ml of a therapeutic or diagnostic composition is delivered to the CSF of a subject per month; e.g., about 20 ml/month or about 40 ml/month. A desired pulsatile delivery regimen may thus be calculated based on this desired volume. By way of example, if a flow rate of 2.4 ml per day is suitable to achieve desired CSF distribution and if it is desired to deliver 20 ml or less per month, the composition may be delivered at a rate of about 0.0017/min for one minute, every four minutes (or 15 times an hour). This would result in delivery of about 0.0255 ml/hour, 0.612 ml/day, or about 18.36 ml/month (assuming 30 days in a month). The rate, duration, and frequency of delivery may be modified as desired to achieve desired distribution and desired delivery volumes.

Preferably, the rate, duration, and frequency of delivery are determined such that an appropriate steady state concentration of therapeutic or diagnostic agent is achieved at desired CSF location. For example, if a therapeutic agent is delivered at an intrathecal location with the intention of having an effect at the brain, it would be desirable for steady state concentrations of the therapeutic agent in the CSF at, for example, the ventricles to be sufficiently high to be effective for treating a disease state. It will be understood that the CSF turnover rate and the tendency for the agent to diffuse out of the CSF may be accounted for in determining appropriate rates, durations, and frequencies of delivery, as well as concentrations of therapeutic agent.

Figure 2:
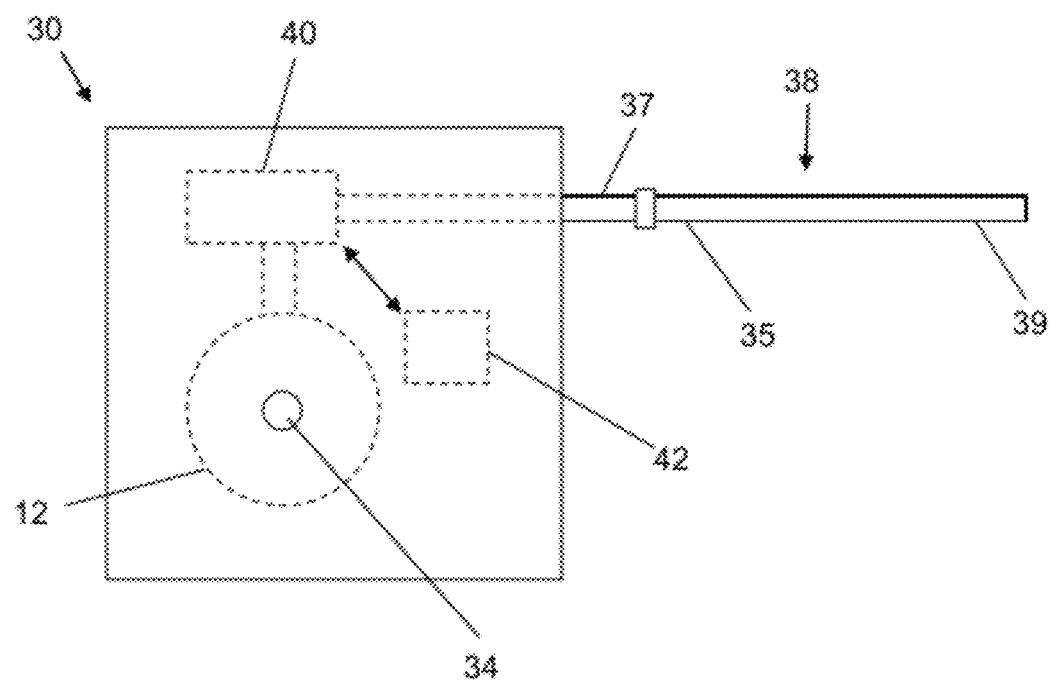
FIG. 2 is a schematic drawing of a side view of a representative infusion device system.

To assist in obtaining such dosage regimens, an infusion system may be employed. An example of an infusion system that may be employed is shown in FIG. 2. The system includes an infusion device 30 having a reservoir 12 for housing a fluid composition and a pump 40 operably coupled to the reservoir 12. The system further includes a catheter 38 having a proximal end 35 coupled to the infusion device 30 and a distal end 39 configured to be implanted in a target location of a subject. Between the proximal end 35 and distal end 39 or at the distal end 39, the catheter 38 has one or more delivery regions (not shown), such as openings, through which the fluid composition may be delivered. The infusion device 30 may have a port 34 into which a hypodermic needle can be inserted to inject the composition into the reservoir 12. The infusion device 30 may have a catheter port 37, to which the proximal end 35 of catheter 38 may be coupled. The catheter port 37 may be operably coupled to reservoir 12. The infusion device 30 may be operated to discharge a predetermined dosage of the pumped fluid into a target region of a subject at a predetermined rate. The infusion device 30 may contain a microprocessor 42 or similar electronics that can be programmed to control the amount and rate of fluid delivery. The programming may be accomplished with an external programmer/control unit via telemetry. With the use of a programmable infusion device 30, dosage regimens may be programmed and tailored for a particular subject. Additionally, different dosages can be programmed for different combinations of fluid compositions. Those skilled in the art will recognize that a programmable infusion device 30 allows for starting conservatively with lower doses and adjusting to a more aggressive dosing scheme, if warranted, based on safety and efficacy factors when used for therapeutic purposes.

Figure 3:
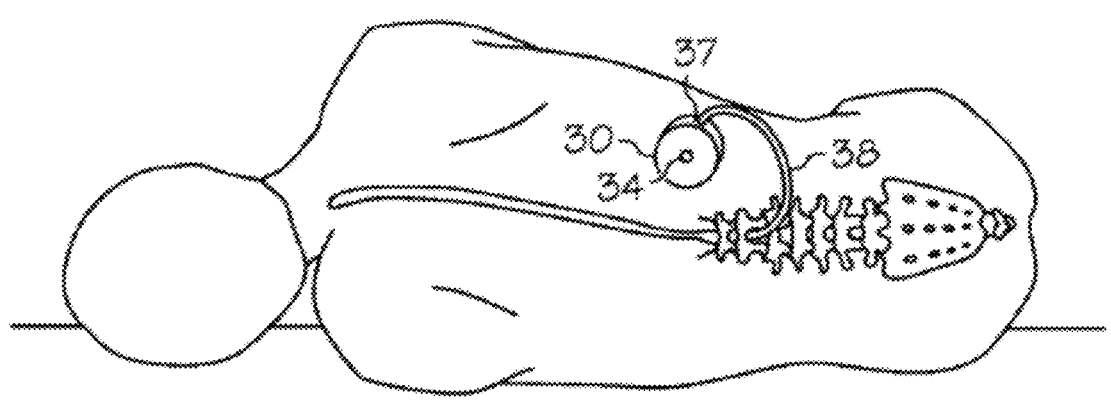
FIG. 3 is a schematic drawing of a view of an infusion device and associated catheter implanted in a patient.

FIG. 3 illustrates an example of an infusion system configured for intrathecal delivery of a composition containing a molecule of interest. As shown in FIG. 3, a system or device 30 may be implanted below the skin of a patient. Preferably the device 30 is implanted in a location where the implantation interferes as little as practicable with activity of the subject in which it is implanted. One suitable location for implanting the device 30 is subcutaneously in the lower abdomen. In various embodiments, catheter 38 is positioned so that the distal end 39 of catheter 38 is located in the subarachnoid space 3 of the spinal cord such that a delivery region (not shown) of catheter is also located within the subarachnoid space 3.

In many embodiments, a composition containing a molecule is administered intrathecally at a low flow rate to achieve distribution of the molecule in the brain. Intrathecal administration provides several advantages to administration directly to the brain or ICV administration. Primarily, intrathecal administration allows one to avoid placement of a catheter or cannula through parenchymal tissue of the brain to reach a desired location or the cerebral ventricle. Accordingly, the subject to which the molecule is delivered is spared a great deal of risk and discomfort with IT delivery relative to ICV delivery. Further, the time involved with surgical procedures for delivering a molecule intrathecally is significantly less than delivering the molecule intracerebroventricularly.

However, in some embodiments, a composition containing a molecule of interest is delivered intraparenchymally or intracerebroventricularly. For example, for ICV delivery, a catheter may be operably coupled to the infusion device and a delivery region of the catheter may be placed in the ventricle.

Figure 4:
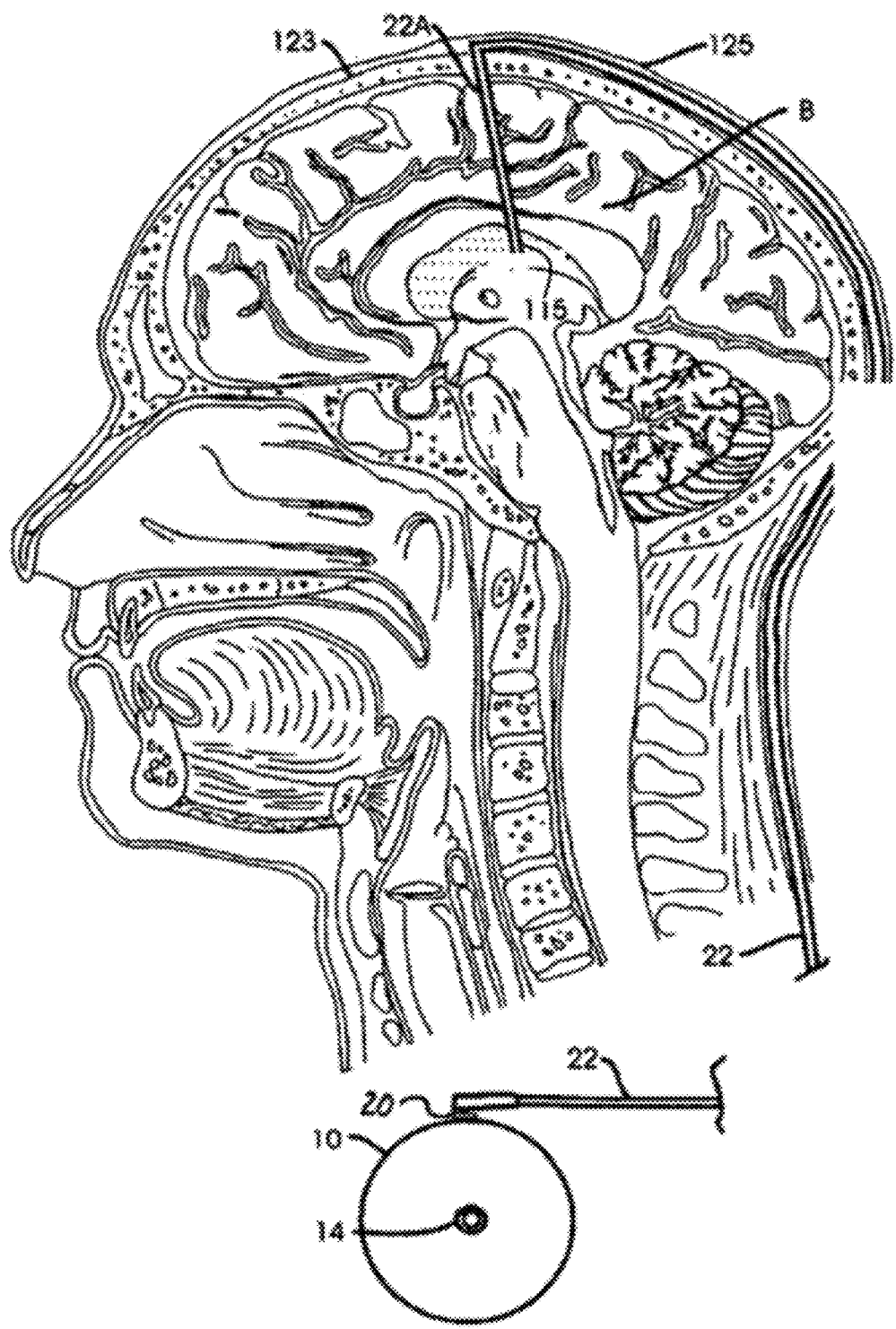
FIG. 4 is a schematic drawing of a view of a section of a patient showing an implanted infusion device and associated catheter implanted.

One suitable system for administering a therapeutic agent to the brain is discussed in U.S. Pat. No. 5,711,316 (Elsberry). Referring to FIG. 4, a system or infusion device 10 may be implanted below the skin of a subject. The device 10 may have a port 14 into which a hypodermic needle can be inserted through the skin to inject a quantity of a composition comprising the molecule of interest. The composition is delivered from device 10 through a catheter port 20 into a catheter 22. Catheter 22 is positioned to deliver the agent to a cerebral ventricle 115 in the brain (B). Device 10 may take the form of the like-numbered device shown in U.S. Pat. No. 4,692,147 (Duggan), assigned to Medtronic, Inc., Minneapolis, Minn., take the form of a SynchroMed II infusion device (Medtronic, Inc.), or take the form of any currently available or future developed infusion device. In the depicted embodiment, the distal end of catheter 22 terminates in a cylindrical hollow tube 22A having a distal end implanted in the ventricle 115 by conventional stereotactic surgical techniques. Tube 22A is surgically implanted through a hole in the skull 123 and catheter 22 is implanted between the skull and the scalp 125 as shown in FIG. 4. Catheter 22 may be coupled to implanted device 10 in the manner shown or in any other suitable manner.

Figure 5:
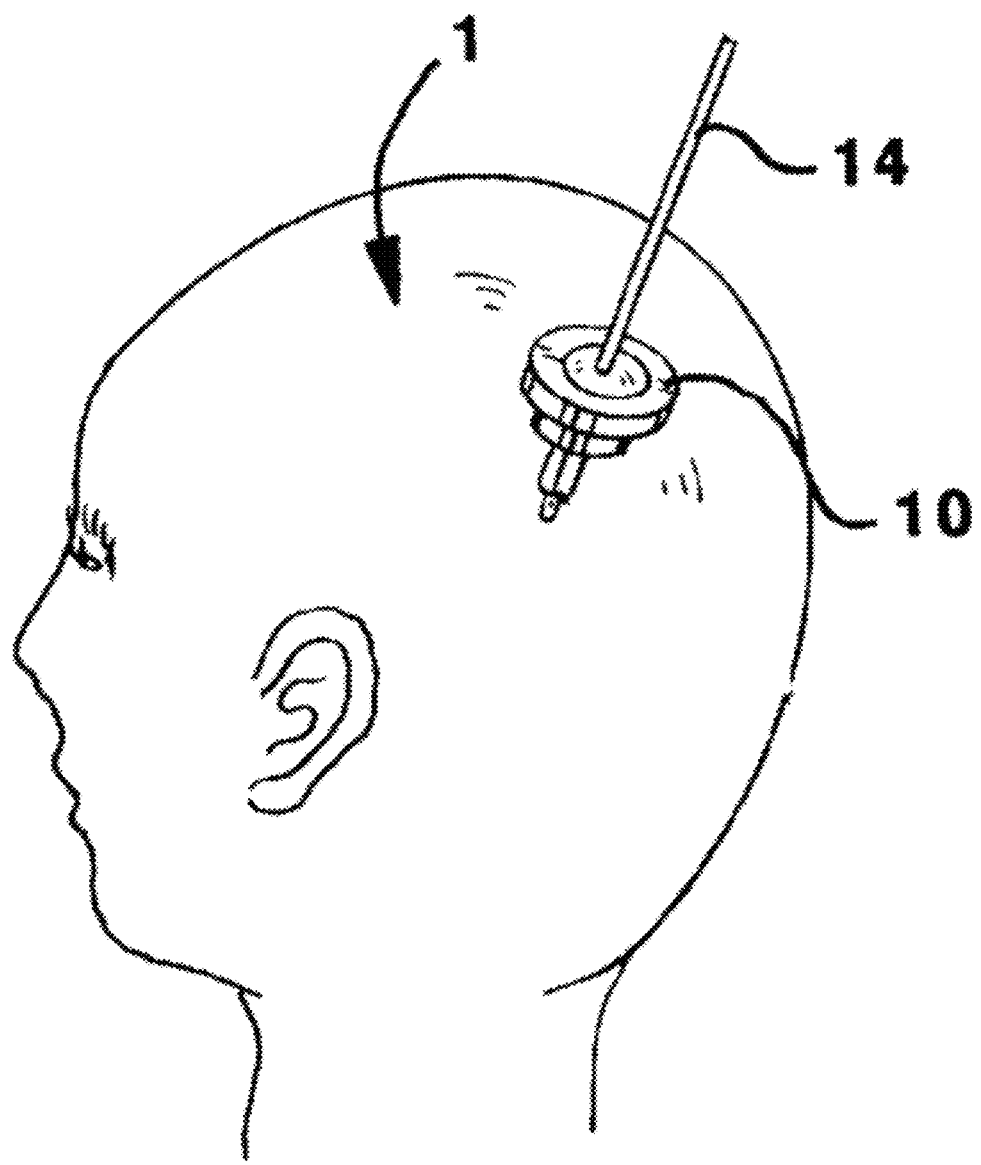
FIG. 5 is a schematic drawing of a view showing an injection port in the environment of a patient.

Referring to FIG. 5, a molecule of interest may be delivered to a subject's CSF via an injection port 10 implanted subcutaneously in the scalp of a patient 1, e.g. as described in U.S. Pat. No. 5,954,687 or otherwise known in the art. A guide catheter 10 may be used to guide an infusion catheter through port 10 to a target location. Of course, an infusion catheter may be directly be inserted through port 10 to the target location. Such ports 10 may also be employed to deliver the molecule intrathecally.

Any other known or developed implantable or external infusion device or port may be employed.

A brief summary of various aspects of methods, systems and devices described herein are presented below:

A $1^{st}$ aspect is a method for delivering a therapeutic or diagnostic molecule to cerebrospinal fluid (CSF) of a brain of a subject that includes administering a liquid formulation comprising the molecule to an CSF-containing intrathecal space of the subject at a flow rate of less than 500 microliters per hour, wherein the liquid formulation is administered for a period of time sufficient to reach a steady state concentration in CSF of the brain, and wherein the molecular weight of the molecule is less than 5 kDa, between 15 kDa and 200 kDa, greater than 200 kDa, or a polypeptide or antisense DNA having a molecular weight of between 5 kDa and 15 kDa.

A $2^{nd}$ aspect is a method of aspect 1, wherein the liquid formulation is administered at a flow rate of less than 200 microliters per hour.

A $3^{rd}$ aspect is a method of aspect 1, wherein the liquid formulation is administered at a flow rate of between about 4 microliters per hour and about 100 microliters per hour.

A $4^{th}$ aspect is a method of aspect 1, wherein the liquid formulation is administered at a flow rate of between about 2 microliters per hour and about 25 microliters per hour.

A $5^{th}$ aspect is a method according to any of aspects 1-4, wherein the liquid formulation is delivered via a catheter having a delivery region placed in the CSF-containing space.

A $6^{th}$ aspect is a method of aspect 5, wherein the CSF-containing space is selected from the group consisting of lumbar intrathecal space, thoracic intrathecal space, and cervical intrathecal space.

A $7^{th}$ aspect is a method according to any of aspects 1-6, wherein the molecule is a therapeutic molecule and wherein the steady state concentration is a therapeutically effective concentration.

An $8^{th}$ aspect is a method according to aspect 7, further comprising administering the liquid formulation at a second slower rate for a period of time sufficient to reduce the concentration of the molecule in the CSF.

A $9^{th}$ aspect is a method according to aspect 8, wherein the liquid formulation is administered via a catheter, and wherein the second slower rate is sufficient to keep the catheter patent.

A $10^{th}$ aspect is a method for broadly distributing a therapeutic or diagnostic molecule in cerebrospinal fluid (CSF) of a subject including administering a liquid formulation comprising the molecule to the CSF at a flow rate of less than 500 microliters per hour, wherein the liquid formulation is administered for a period of time sufficient to reach a steady state concentration in the CSF, and wherein the molecular weight of the molecule is less than 5 kDa, between 15 kDa and 200 kDa, greater than 200 kDa, or a polypeptide or antisense DNA having a molecular weight of between 5 kDa and 15 kDa.

An $11^{th}$ aspect is a method of aspect 10, wherein the liquid formulation is administered at a flow rate of less than 200 microliters per hour.

A $12^{th}$ aspect is a method of aspect 10, wherein the liquid formulation is administered at a flow rate of between about 4 microliters per hour and about 100 microliters per hour.

A $13^{th}$ aspect is a method of aspect 10, wherein the liquid formulation is administered at a flow rate of between about 2 microliters per hour and about 25 microliters per hour.

A $14^{th}$ aspect is a method of any of aspects 10-13, wherein the liquid formulation is delivered via a catheter having a delivery region placed in the CSF.

A $15^{th}$ aspect is a method according to aspect 14, wherein the delivery region is positioned in a CSF location selected from the group consisting of lumbar intrathecal space, thoracic intrathecal space, cervical intrathecal space, cisterna magna, subdural space, subarachnoid space, and the intracerebroventricular space.

A $16^{th}$ aspect is a method according to any of aspects 10-15, wherein the molecule is a therapeutic molecule and wherein the steady state concentration is a therapeutically effective concentration.

A $17^{th}$ aspect is a method according to aspect 16, further comprising administering the liquid formulation at a second slower rate for a period of time sufficient to reduce the concentration of the molecule in the CSF.

An $18^{th}$ aspect is a method according to aspect 17, wherein the liquid formulation is administered via a catheter, and wherein the second slower rate is sufficient to keep the catheter patent.

A $19^{th}$ aspect is a system comprising: (i) a liquid formulation comprising a therapeutic or diagnostic molecule, wherein the molecular weight of the molecule is less than 5 kDa, between 15 kDa and 200 kDa, greater than 200 kDa, or a polypeptide or antisense DNA having a molecular weight of between 5 kDa and 15 kDa; and (ii) a programmable implantable infusion device having (a) a reservoir configured to house the liquid formulation, (b) an outlet in fluid communication with the reservoir, (c) a drive mechanism configured to control the rate at which the liquid formulation is delivered to the outlet from the reservoir; (d) electronics operably coupled to the drive mechanism, wherein the electronics are programmed with instructions that cause the liquid formulation to be delivered from the reservoir to the outlet at a flow rate of less than 500 microliters per hour for a period of time sufficient to reach a steady state concentration in a subject's cerebrospinal fluid (CSF) if the liquid formulation is administered to a CSF-containing compartment of the subject.

A $20^{th}$ aspect is a system of aspect 19, wherein instructions cause the liquid formulation to be administered at a flow rate of less than 200 microliters per hour.

A $21^{st}$ aspect is a system of aspect 19, wherein instructions cause the liquid formulation to be administered at a flow rate of between about 4 microliters per hour and about 100 microliters per hour.

A 22$^{nd}$ aspect is a system of aspect 19, wherein instructions cause the liquid formulation to be administered at a flow rate of between about 2 microliters per hour and about 25 microliters per hour.

A 23$^{rd}$ aspect is a system of any of aspects 19-22, further comprising a catheter operably couplable to the outlet for delivering the liquid formulation to a target location of subject's CSF.

A 24$^{th}$ aspect is a system comprising: (i) a liquid formulation comprising a therapeutic or diagnostic molecule, wherein the molecular weight of the molecule is less than 5 kDa, between 15 kDa and 200 kDa, greater than 200 kDa, or a polypeptide or antisense DNA having a molecular weight of between 5 kDa and 15 kDa; and (ii) a programmable implantable infusion device having (a) a reservoir configured to house the liquid formulation, (b) an outlet in fluid communication with the reservoir, (c) a drive mechanism configured to control the rate at which the liquid formulation is delivered to the outlet from the reservoir; (d) electronics operably coupled to the drive mechanism, wherein the electronics are configured to cause the liquid formulation to be delivered from the reservoir to the outlet at a flow rate of less than 500 microliters per hour for a period of time sufficient to reach a steady state concentration in a subject's cerebrospinal fluid (CSF) if the liquid formulation is administered to a CSF-containing compartment of the subject.

A 25$^{th}$ aspect is a system according to aspect 24, wherein the electronics are configured to cause the liquid formulation to be administered at a flow rate of less than 200 microliters per hour.

A 26$^{th}$ aspect is a system according to aspect 24, wherein the electronics are configured to cause the liquid formulation to be administered at a flow rate of between about 4 microliters per hour and about 100 microliters per hour.

A 27$^{th}$ aspect is a system according to aspect 24, wherein the electronics are configured to cause the liquid formulation to be administered at a flow rate of between about 2 microliters per hour and about 25 microliters per hour.

A 28$^{th}$ aspect is a system according to any of aspects 24-27, further comprising a catheter operably couplable to the outlet for delivering the liquid formulation to a target location of subject's CSF.

A 29$^{th}$ aspect is a method for delivering a therapeutic or diagnostic molecule to the brain of a subject, comprising administering a liquid formulation comprising the molecule to an intrathecal space of the subject at a flow rate of less than 500 microliters per hour.

A 30$^{th}$ aspect is a method of aspect 29, wherein the liquid formulation is administered at a flow rate of less than 200 microliters per hour.

A 31$^{st}$ aspect is a method of aspect 29, wherein the liquid formulation is administered at a flow rate of between about 4 microliters per hour and about 100 microliters per hour.

A 32$^{nd}$ aspect is a method according to any of aspects 29-31, wherein administering the liquid formulation comprises delivering the liquid formulation from an implantable infusion device or an external infusion device.

A 33$^{rd}$ aspect is a method according to any of aspects 29-32, wherein the molecule has a molecular weight of less than 5 kDa.

A 34$^{th}$ aspect is a method according to any of aspects 29-32, wherein the molecule has a molecular weight of greater than 5 kDa.

A 35$^{th}$ aspect is a method according to any of aspects 29-32, wherein the molecule has a molecular weight of between about 5 kDa and about 15 kDa.

A 36$^{th}$ aspect is a method according to any of aspects 29-32, wherein the molecule has a molecular weight of between about 15 kDa and about 200 kDa.

A 37$^{th}$ aspect is a method according to any of aspects 29-32, wherein the molecule has a molecular weight of greater than about 200 kDa.

A 38$^{th}$ aspect is a method according to any of aspects 29-37, wherein the liquid formulation is delivered via a catheter, wherein the catheter has a delivery region, and wherein the deliver region is placed in the subject's lumbar intrathecal space, thoracic intrathecal space, or cervical intrathecal space.

A 39$^{th}$ aspect is a method according to any of aspects 29-38, wherein the molecule is a therapeutic molecule and is delivered at a rate, frequency, duration, location and concentration suitable to achieve a therapeutically effective steady state concentration.

A 40$^{th}$ aspect is a method according to any of aspects 29-39, with the proviso that the molecule is not an interfering RNA molecule.

A 41$^{st}$ aspect is a method according to any of aspects 29-39, with the proviso that the molecule is not a inhibitory RNA molecule configured to inhibit expression of a Huntington protein.

A 42$^{nd}$ aspect is a method for broadly distributing a therapeutic or diagnostic molecule in cerebral spinal fluid of a subject, comprising administering a liquid formulation comprising the molecule to the cerebrospinal fluid of the subject at a flow rate of less than 500 microliters per hour.

A 43$^{rd}$ aspect is a method according to aspect 42, wherein the liquid formulation is administered at a flow rate of less than 200 microliters per hour.

A 44$^{th}$ aspect is a method according to aspect 42, wherein the liquid formulation is administered at a flow rate of between about 4 microliters per hour and about 100 microliters per hour.

A 45$^{th}$ aspect is a method according to any of aspects 42-44, wherein administering the liquid formulation comprises delivering the liquid formulation from an implantable infusion device or an external infusion device.

A 46$^{th}$ aspect is a method according to any of aspects 42-45, wherein the molecule has a molecular weight of less than 5 kDa.

A 47$^{th}$ aspect is a method according to any of aspects 42-45, wherein the molecule has a molecular weight of greater than 5 kDa.

A 48$^{th}$ aspect is a method according to any of aspects 42-45, wherein the molecule has a molecular weight of between about 5 kDa and about 15 kDa.

A 49$^{th}$ aspect is a method according to any of aspects 42-45, wherein the molecule has a molecular weight of between about 15 kDa and about 200 kDa.

A 50$^{th}$ aspect is a method according to any of aspects 42-45, wherein the molecule has a molecular weight of greater than about 200 kDa.

A 51$^{st}$ aspect is a method according to any of aspects 42-50, wherein the molecule is delivered via a catheter having a delivery region, wherein the delivery region is placed in the subject's intrathecal space.

A 52$^{nd}$ aspect is a method according to any of aspects 42-51, wherein the molecule is a therapeutic molecule and is delivered at a rate, frequency, duration, location and concentration suitable to achieve a therapeutically effective steady state concentration.

A 53$^{rd}$ aspect is a method according to any of aspects 42-52, with the proviso that the molecule is not an interfering RNA molecule.

A 54th aspect is a method according to any of aspects 42-52, with the proviso that the molecule is not a inhibitory RNA molecule configured to inhibit expression of a Huntington protein.

A 55th aspect is a system comprising: (i) a liquid formulation comprising a therapeutic or diagnostic molecule, with the proviso that the molecule is not an interfering RNA molecule or that the molecule is not a inhibitory RNA molecule configured to inhibit expression of a Huntington protein; and (ii) a programmable implantable infusion device having (a) a reservoir configured to house the liquid formulation, (b) an outlet in fluid communication with the reservoir, (c) a drive mechanism configured to control the rate at which the liquid formulation is delivered to the outlet from the reservoir; (d) electronics operably coupled to the drive mechanism, wherein the electronics are programmed with instructions that cause the liquid formulation to be delivered from the reservoir to the outlet at a flow rate of less than 500 microliters per hour for a period of time sufficient to reach a steady state concentration in a subject's cerebrospinal fluid (CSF) if the liquid formulation is administered to a CSF-containing compartment of the subject.

A 56th aspect is a system according to aspect 55, wherein instructions cause the liquid formulation to be administered at a flow rate of less than 200 microliters per hour.

A 57th aspect is a system according to aspect 55, wherein instructions cause the liquid formulation to be administered at a flow rate of between about 4 microliters per hour and about 100 microliters per hour.

A 58th aspect is a system according to aspect 55, wherein instructions cause the liquid formulation to be administered at a flow rate of between about 2 microliters per hour and about 25 microliters per hour.

A 59th aspect is a system according to any of aspects 55-58, further comprising a catheter operably couplable to the outlet for delivering the liquid formulation to a target location of subject's CSF.

A 60th aspect is a system comprising: (i) a liquid formulation comprising a therapeutic or diagnostic molecule, with the proviso that the molecule is not a inhibitory RNA molecule or that the molecule is not a inhibitory RNA molecule configured to inhibit expression of a Huntington protein; and (ii) a programmable implantable infusion device having (a) a reservoir configured to house the liquid formulation, (b) an outlet in fluid communication with the reservoir, (c) a drive mechanism configured to control the rate at which the liquid formulation is delivered to the outlet from the reservoir; (d) electronics operably coupled to the drive mechanism, wherein the electronics are configured to cause the liquid formulation to be delivered from the reservoir to the outlet at a flow rate of less than 500 microliters per hour for a period of time sufficient to reach a steady state concentration in a subject's cerebrospinal fluid (CSF) if the liquid formulation is administered to a CSF-containing compartment of the subject.

A 61st aspect is a system according to aspect 60, wherein the electronics are configured to cause the liquid formulation to be administered at a flow rate of less than 200 microliters per hour.

A 62nd aspect is a system according to aspect 60, wherein the electronics are configured to cause the liquid formulation to be administered at a flow rate of between about 4 microliters per hour and about 100 microliters per hour.

A 63rd aspect is a system according to aspect 60, wherein the electronics are configured to cause the liquid formulation to be administered at a flow rate of between about 2 microliters per hour and about 25 microliters per hour.

A 64th aspect is a system according to any of aspects 60-63, further comprising a catheter operably couplable to the outlet for delivering the liquid formulation to a target location of subject's CSF.

In the following, non-limiting examples of the methods described herein are presented.

EXAMPLES

CADD ambulatory infusion pumps were used to deliver gadolinium (Gd) labeled diethylene triamine pentaacetic acid (DTPA) or Gd-labeled albumin to rhesus monkeys, either intrathecally or intracerebroventricularly. Distribution of the Gd-labeled agents was tracked in-life via magnetic resonance imaging (MRI).

The Gd-DPTA has a molecular weight of about 600 Daltons and serves as a proxy for small molecule agents. The Gd-albumin had a molecular weight of about 74 kDa and serves as a proxy for mid-sized biologics.

For the Gd-DTPA studies, various concentrations of the Gd-DTPA were administered. The Gd-DTPA was administered intrathecally at L2 or intracerebroventricularly via a lateral ventricle at a variety of flow rates. Within a given monkey various flow rates were tested, followed by a washout period with phosphate buffered saline (PBS). An example study design that was used is presented below in Table 2:

TABLE 2

Flow rates and agents used for intrathecal Gd-DTPA

| | Study Day | | | | | | | | | |
|---|---|---|---|---|---|---|---|---|---|---|
| | 1 | 4 | 7 | 12 | 15 | 20 | 23 | 28 | 31 | 36 |
| Test Article | PBS | Gd-DTPA | PBS | Gd-DTPA | PBS | Gd-DPTA | PBS | Gd-DTPA | PBS | Gd-DPTA |
| Flow Rate (ml/day) | 0.096 | 0.096 | 0.096 | 0.384 | 0.096 | 1.2 | 0.096 | 2.4 | 0.096 | 0.096 |

Figure 6:
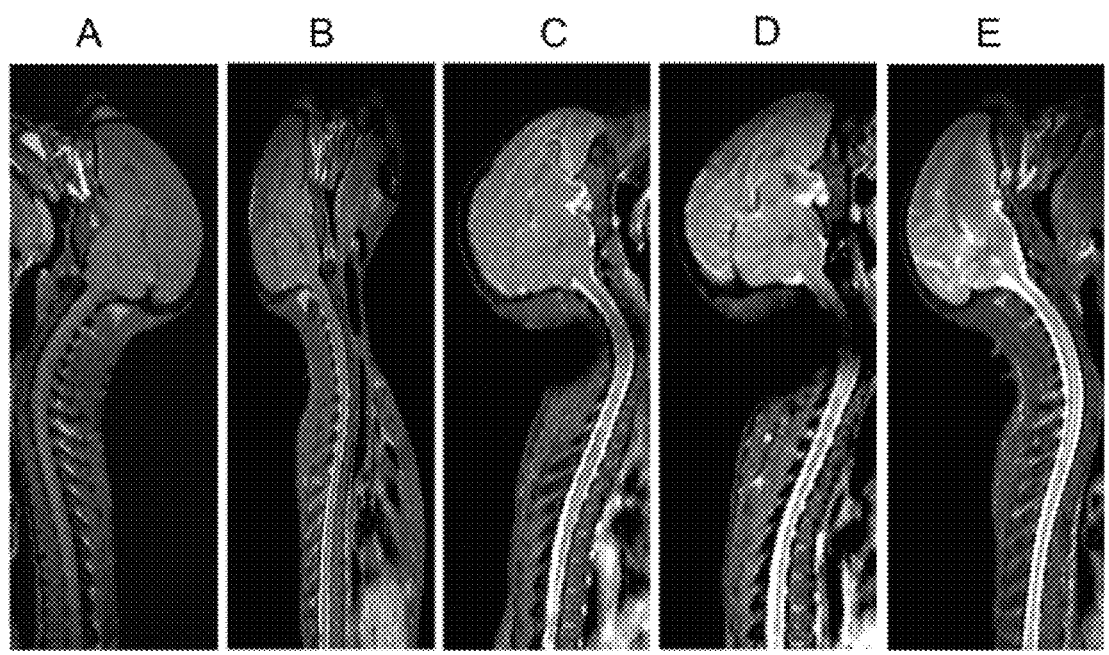
FIGS. 6A-E are MRI images of a rhesus monkey receiving intrathecal administration of Gd-DTPA at the lumbar level (L2) at various flow rates: (A) prior to infusion of Gd-DTPA, (B) 0.1 ml/day, (C) 0.4 ml/day, (D) 1.2 ml/day and (E) 2.4 ml/day.

At lower concentrations (e.g., 17.5 mg/ml, 5.8 mg/ml, and 2.9 mg/ml), Gd-DTPA infused at 0.4 mL/day was not appreciably detectable by MRI. However at 70 mg/ml concentration, Gd-DTPA was detectable and was observed to be broadly distributed throughout the CSF. While not detectable at lower concentrations, it is believed that the distribution of the lower concentration agent was similar to that observed at the 70 mg/ml concentration at similar flow rates. FIG. 6 shows MRI images obtained from monkeys receiving Gd-DTPA at 0.1 ml/day (B), 0.4 ml/day (C), 1.2 mL/day (D), and 2.4 ml/day (E). FIG. 6A is an MRI image of the same monkey prior to infusion of Gd-DTPA. As shown in FIG. 6, broad distribution was observed at all flow rates of about 0.4 ml/day or greater. At the 2.4 ml/day (100 microliters per hour) flow rate the amount of Gd-DTPA delivered was the greatest, and thus the signal was most intense.

Figure 7:
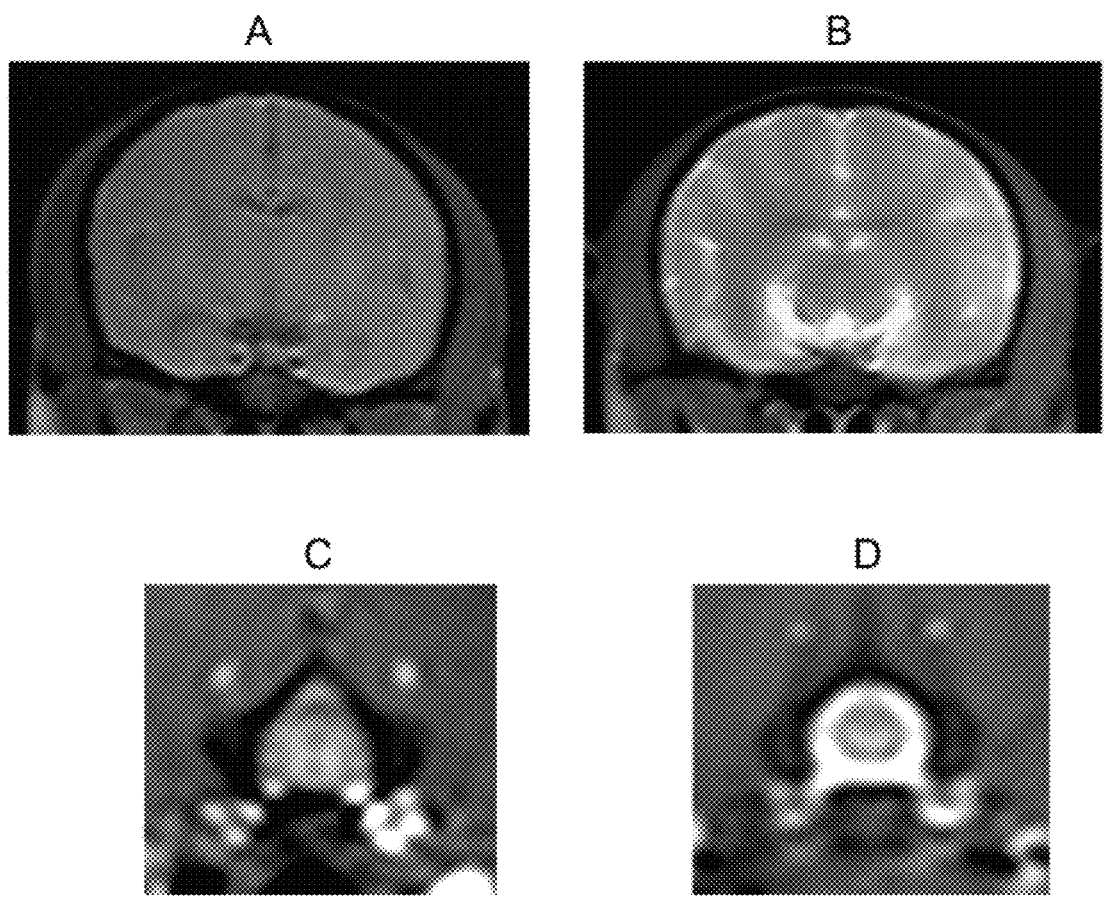
FIGS. 7A-D are MRI images (axial views showing the brain A-B, and spinal cord C-D) of a rhesus monkey receiving 70 mg/ml Gd-DTPA at a rate of 2.4 ml/day (100 microliters/hour) intrathecally at L2 (B, D).

As shown in FIG. 7B, which is an axial view of the monkey receiving 70 mg/ml Gd-DTPA at a rate of 2.4 ml/day (100 microliters/hour) intrathecally at L2, the Gd-DTPA appears to be taken up by the parenchymal tissue of the brain of the monkey (FIG. 7A is an axial view of the monkey's brain prior to infusion of Gd-DTPA). These results suggest not only that the agent is broadly distributed in the CSF at low flow rates but also that it is able to be taken up by the brain tissue. As discussed below with regard to FIG. 10, which shows images of various MRI slices of monkeys to which Gd-albumin were delivered, a similar broad CNS tissue distribution of Gd-DPTA was observed (data not shown).

Interestingly, FIG. 7D, which is an axial view including the spinal cord of the same monkey shown in FIGS. 7A-B, shows that the Gd-DTPA has distributed in a circumferential manner around the intrathecal space under steady state conditions (FIG. 7C shows the same monkey prior to administration of the Gd-DTPA). Such circumferential distribution has not been reported by others, and it was thought that an agent administered intrathecally would remain in a column.

Figure 8:
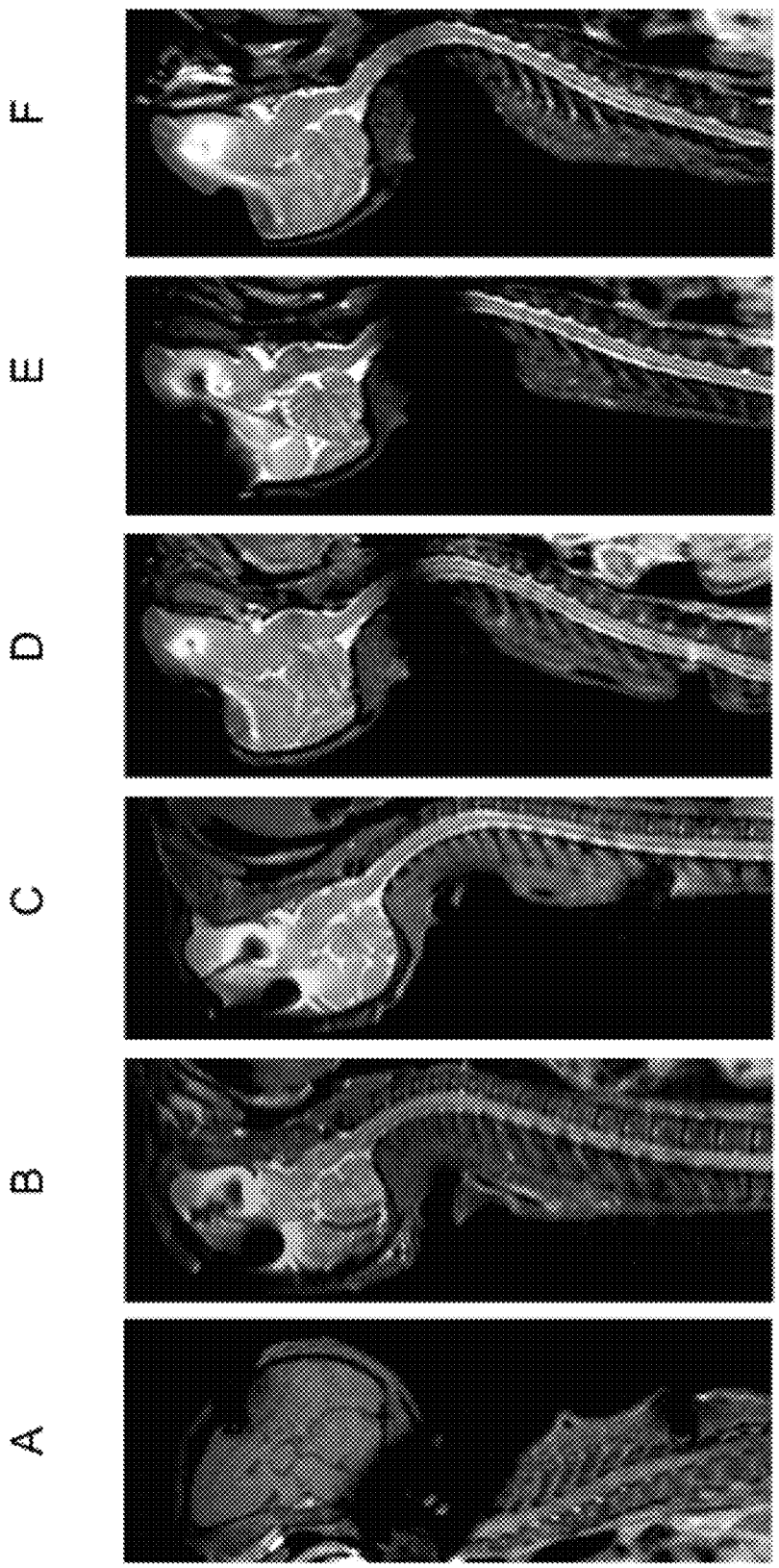
FIGS. 8A-F are MRI images of rhesus monkeys receiving various concentrations of Gd-DPTA intracerebroventricularly at various flow rates: (A) prior to infusion of the Gd-DPTA; (B) 486 mg/ml at 0.048 ml/day; (C) 280 mg/ml at 0.1 ml/day; (D) 70 mg/ml at 0.4 ml/day; (E) 35 mg/ml at 0.8 ml/day; (F) 22 mg/ml at 1.2 ml/day.

Referring now to FIGS. 8A-F, MRI images of a rhesus monkey receiving various concentrations of Gd-DPTA intracerebroventricularly at various flow rates are shown. FIG. 8A is an MRI image of a monkey receiving PBS prior to infusion of the Gd-DPTA. FIG. 8B is an MRI image of a monkey receiving 486 mg/ml at 0.048 ml/day. FIG. 8C is an MRI image of a monkey receiving 280 mg/ml at 0.1 ml/day. FIG. 8D is an MRI image of a monkey receiving 70 mg/ml at 0.4 ml/day. FIG. 8E is an MRI image of a monkey receiving 35 mg/ml at 0.8 ml/day. FIG. 8F is an MRI image of a monkey receiving 22 mg/ml at 1.2 ml/day. As shown in the figure, the Gd-DTPA is broadly distributed in the CSF, including in the intrathecal space at flow rates of about 0.05 ml/day or greater. Accordingly, broad distribution appears to be achievable at low flow rates, regardless of the CSF site of administration.

Figure 9:
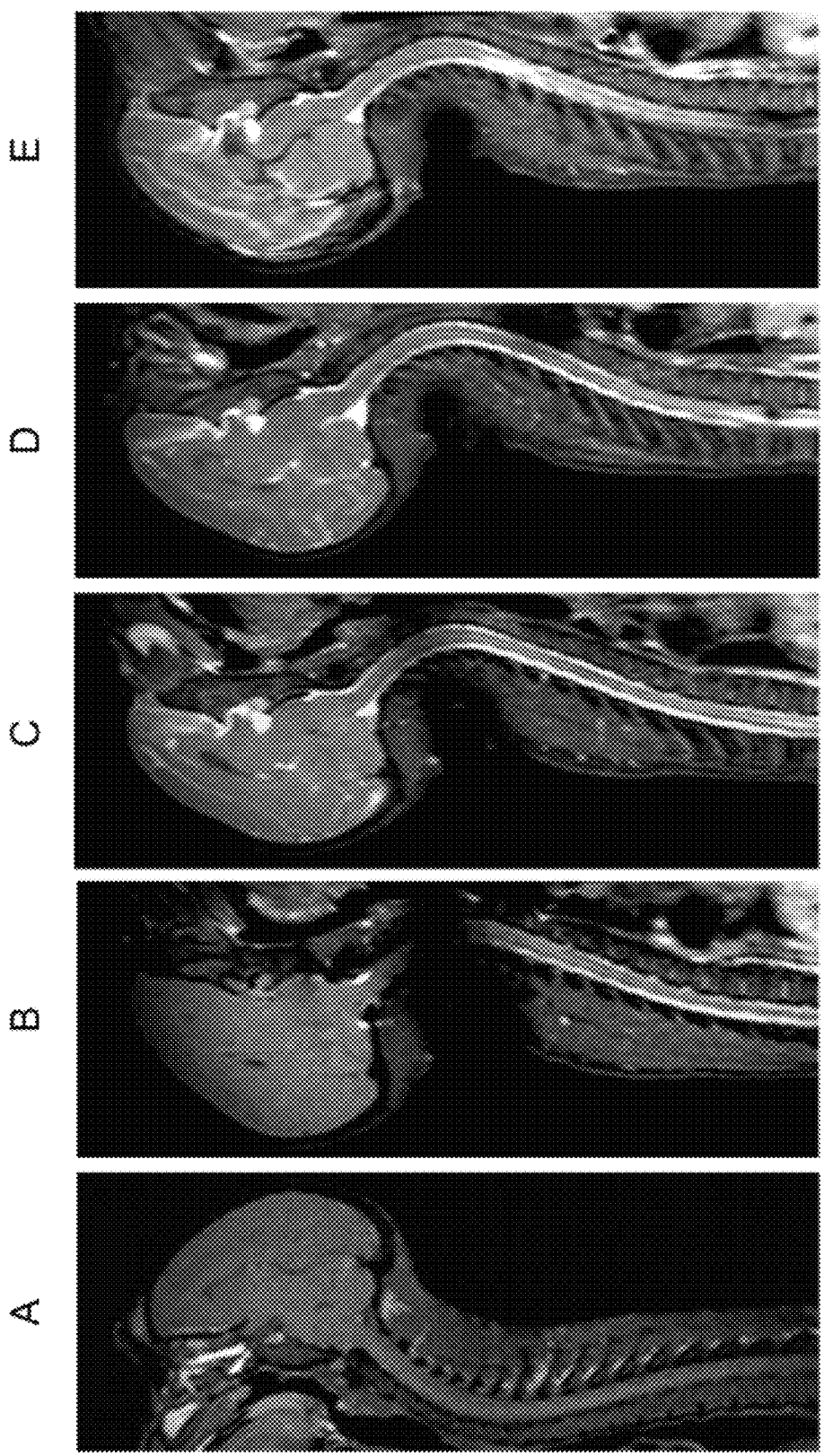
FIGS. 9A-E are MRI images of a rhesus monkeys receiving various concentrations of Gd-albumin intrathecally at various flow rates: (A) prior to infusion of the Gd-albumin; (B) 100 mg/ml at 0.1 ml/day; (C) 100 mg/ml at 0.4 ml/day; (D) 34 mg/ml at 1.2 ml/day; and (E) 17 mg/ml at 2.4 ml/day.

For the Gd-albumin studies, various concentrations of the Gd-albumin were administered intrathecally at L2 at various flow rates. FIGS. 9A-E are MRI images of rhesus monkeys receiving intrathecal Gd-albumin. FIG. 9A shows a rhesus monkeys receiving intrathecal PBS prior to infusion of the Gd-albumin. FIG. 9B shows a rhesus monkey receiving intrathecal 100 mg/ml Gd-albumin at 0.1 ml/day. FIG. 9C shows a rhesus monkey receiving intrathecal 100 mg/ml Gd-albumin at 0.4 ml/day. FIG. 9D shows a rhesus monkey receiving intrathecal 34 mg/ml Gd-albumin at 1.2 ml/day. FIG. 9E shows a rhesus monkey receiving intrathecal 17 mg/ml Gd-albumin at 2.4 ml/day. As shown, a sufficiently strong signal was observed at all concentrations, with greater distribution observed with higher infusion rates. However, even at low rates of infusion distribution was seen throughout the spinal intrathecal space (see 9B, 0.1 ml/day) and within the CSF surrounding the brain (see 9C, 0.4 ml/day).

Figure 10:
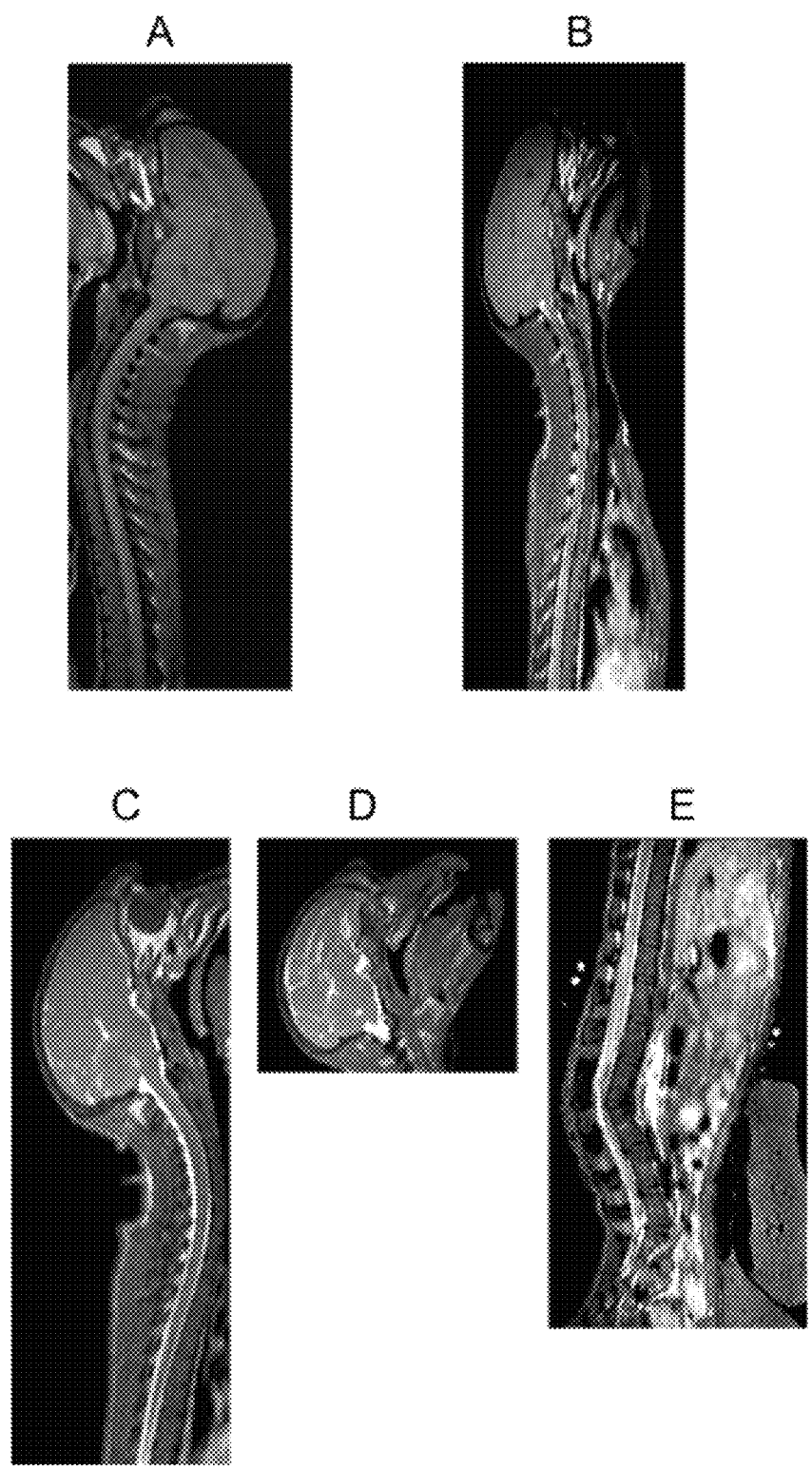
FIGS. 10A-E are MRI images of a rhesus monkey receiving 100 mg/ml Gd-albumin intrathecally at various flow rates: (A) prior to infusion of Gd-albumin; (B) 0.1 ml/day; (C) 2.4 ml/day.

FIG. 10 shows various MRI slices revealing that Gd-albumin was detectable throughout the CSF-containing compartments of the monkey. FIG. 10A is an MRI image prior to infusion of Gd-albumin; FIG. 10B is an image of the monkey while receiving 100 mg/ml at 0.1 ml/day; FIG. 10C is an image of the monkey while receiving 100 mg/ml at 2.4 ml/day; FIG. 10D is a higher magnification view of the brain of the image presented in FIG. 10C; and FIG. 10E is a higher magnification view of the spinal region of the image presented in FIG. 10C.

Figure 11:
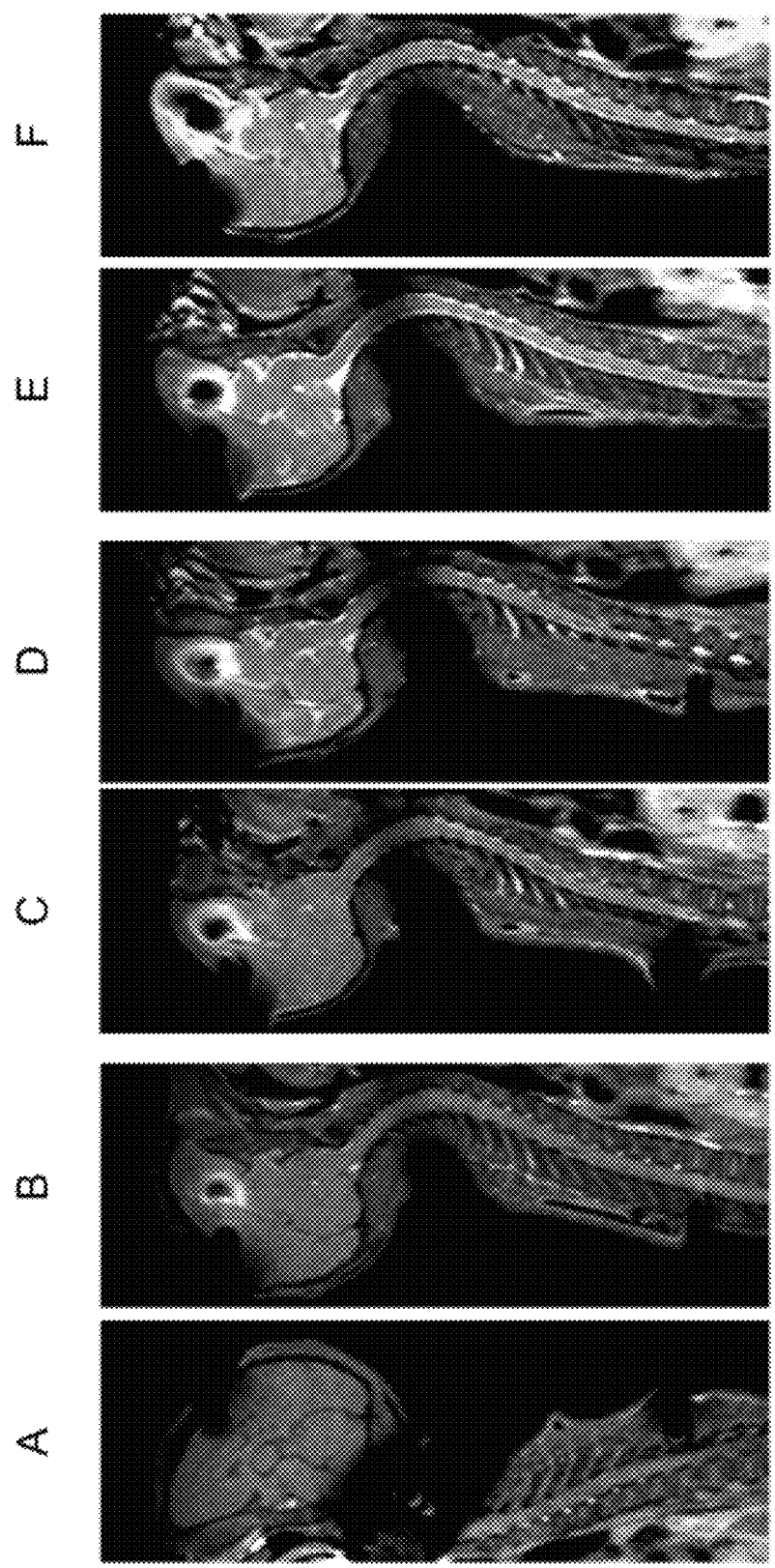
FIGS. 11A-F are MRI images of a rhesus monkey receiving various concentrations of Gd-albumin intracerebroventricularly at various flow rates: (A) prior to infusion; (B) 100 mg/ml at 0.1 ml/day at one day of infusion; (C) 100 mg/ml at 0.4 ml/day at one day of infusion; (D) 100 mg/ml at 0.4 ml/day at three days of infusion; (E) 100 mg/ml at 0.8 ml/day at one day of infusion; and (F) 64 mg/ml at 1.2 ml/day at one day of infusion.

Referring now to FIGS. 11A-F, MRI images of a rhesus monkey receiving various concentrations of Gd-albumin intracerebroventricularly at various flow rates are shown. FIG. 11A is an MRI image of a monkey receiving PBS prior to infusion of the Gd-albumin. FIG. 11B is an MRI image of a monkey receiving 100 mg/ml at 0.1 ml/day at one day of infusion. FIG. 11C is an MRI image of a monkey receiving 100 mg/ml at 0.4 ml/day at one day of infusion. FIG. 11D is an MRI image of a monkey receiving 100 mg/ml at 0.4 ml/day at three days of infusion. FIG. 11E is an MRI image of a monkey receiving 100 mg/ml at 0.8 ml/day at one day of infusion. FIG. 11F is an MRI image of a monkey receiving 64 mg/ml at 1.2 ml/day at one day of infusion. As shown in FIG. 11D, broader distribution is observed after three days of infusion relative to one day of infusion (compare to FIG. 11C). Similar increased distribution was observed at three days relative to one day at other infusion rates (data not shown). At infusion rates of about 0.4 ml/day and greater, distribution in the spinal intrathecal space was observed.

Like the small molecules (Gd-DTPA), large molecules (Gd-albumin) are also broadly distributed following infusion into the CSF at low flow rates.

Thus, embodiments of the METHODS FOR DISTRIBUTING AGENTS TO AREAS OF BRAIN are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A method comprising:
   selecting a subject for which delivery of a therapeutic or diagnostic molecule to cerebrospinal fluid (CSF) of a brain is desired; and
   administering a liquid formulation comprising the molecule to an CSF-containing intrathecal space of the subject at a flow rate of less than 500 microliters per hour, wherein the liquid formulation is administered for a period of time sufficient to reach a steady state concentration in CSF of the brain, and wherein the molecular weight of the molecule is less than 5 kDa, between 15 kDa and 200 kDa, greater than 200 kDa, or a polypeptide or antisense DNA having a molecular weight of between 5 kDa and 15 kDa, and wherein the molecule is generally distributed throughout at least most of the CSF of the brain at therapeutically or diagnostically effective concentrations.

2. A method according to claim 1, wherein the liquid formulation is administered at a flow rate of less than 200 microliters per hour.

3. A method according to claim 1, wherein the liquid formulation is administered at a flow rate of between about 4 microliters per hour and about 100 microliters per hour.

4. A method according to claim 1, wherein the liquid formulation is administered at a flow rate of between about 2 microliters per hour and about 25 microliters per hour.

5. A method according to claim 1, wherein the liquid formulation is delivered via a catheter having a delivery region placed in the CSF-containing space.

6. A method according to claim 5, wherein the CSF-containing space is selected from the group consisting of lumbar intrathecal space, thoracic intrathecal space, and cervical intrathecal space.

7. A method according to claim 1, further comprising administering the liquid formulation at a second slower rate for a period of time sufficient to reduce the concentration of the molecule in the CSF.

8. A method according to claim 7, wherein the liquid formulation is administered via a catheter, and wherein the second slower rate is sufficient to keep the catheter patent.

9. A method comprising:
  selecting a subject for which broad distribution of a therapeutic or diagnostic molecule in cerebrospinal fluid (CSF) of the subject is desired; and
  administering a liquid formulation comprising the molecule to the CSF at a flow rate of less than 500 microliters per hour, wherein the liquid formulation is administered for a period of time sufficient to reach a steady state concentration in the CSF, and wherein the molecular weight of the molecule is less than 5 kDa, between 15 kDa and 200 kDa, greater than 200 kDa, or a polypeptide or antisense DNA having a molecular weight of between 5 kDa and 15 kDa and wherein the molecule is generally distributed throughout at least most of the CSF of the brain at therapeutically or diagnostically effective concentrations.

10. A method according to claim 9, wherein the liquid formulation is administered at a flow rate of less than 200 microliters per hour.

11. A method according to claim 9, wherein the liquid formulation is administered at a flow rate of between about 4 microliters per hour and about 100 microliters per hour.

12. A method according to claim 9, wherein the liquid formulation is administered at a flow rate of between about 2 microliters per hour and about 25 microliters per hour.

13. A method according to claim 9, wherein the liquid formulation is delivered via a catheter having a delivery region placed in the CSF.

14. A method according to claim 13, wherein the delivery region is positioned in a CSF location selected from the group consisting of lumbar intrathecal space, thoracic intrathecal space, cervical intrathecal space, cisterna magna, subdural space, subarachnoid space, and the intracerebroventricular space.

15. A method according to claim 9, further comprising administering the liquid formulation at a second slower rate for a period of time sufficient to reduce the concentration of the molecule in the CSF.

16. A method according to claim 15, wherein the liquid formulation is administered via a catheter, and wherein the second slower rate is sufficient to keep the catheter patent.

17. A method according to claim 14, wherein the delivery region is positioned in the intracerebroventricular space.

18. A method according to claim 9, wherein administering the liquid formulation comprising the molecule to the CSF comprises administering the liquid formulation to a lumbar intrathecal space.

19. A method according to claim 1, wherein administering the liquid formulation comprising the molecule to the CSF-containing intrathecal space comprises administering the liquid formulation to a lumbar intrathecal space.

* * * * *